United States Patent [19]
Pless

[11] Patent Number: 5,447,518
[45] Date of Patent: Sep. 5, 1995

[54] METHOD AND APPARATUS FOR PHASE RELATED CARDIAC DEFIBRILLATION

[75] Inventor: Benjamin D. Pless, Menlo Park, Calif.

[73] Assignee: Ventritex, Inc., Sunnyvale, Calif.

[21] Appl. No.: 114,574

[22] Filed: Aug. 31, 1993

[51] Int. Cl.⁶ ............................................ A61N 1/39
[52] U.S. Cl. ........................................................ 607/5
[58] Field of Search .................... 607/5, 7, 25, 26; 128/696, 702–705

[56] References Cited

U.S. PATENT DOCUMENTS

| | | |
|---|---|---|
| 3,706,313 | 12/1972 | Milani et al. |
| 3,924,641 | 12/1975 | Weiss. |
| 4,300,567 | 11/1981 | Kolenik et al. ............ 607/5 |
| 4,384,585 | 5/1983 | Zipes. |
| 4,637,397 | 1/1987 | Jones et al. |
| 4,708,145 | 11/1987 | Tacher, Jr. et al. |
| 4,768,512 | 9/1988 | Imran. |
| 4,850,357 | 7/1989 | Bach, Jr. |
| 4,967,747 | 11/1990 | Carroll et al. ............ 607/5 |
| 4,998,531 | 3/1991 | Bocchi et al. |
| 5,007,422 | 4/1991 | Pless et al. |
| 5,279,291 | 1/1994 | Adams et al. ............ 607/5 |
| 5,304,139 | 4/1994 | Adams et al. ............ 607/5 X |

FOREIGN PATENT DOCUMENTS

| | | | |
|---|---|---|---|
| 9218198 | 10/1992 | WIPO | 607/5 |
| 9319809 | 10/1993 | WIPO | 607/5 |
| 9320891 | 10/1993 | WIPO | 607/5 |

OTHER PUBLICATIONS

"Ventricular Defibrillation Using Biphasic Waveforms: the Importance of Phasic Duration" (Tang, et al) JACC vol. 13, No. 1, pp. 207–214, Jan. 1989.

*Primary Examiner*—William E. Kamm
*Assistant Examiner*—Jeffrey R. Jastrzab
*Attorney, Agent, or Firm*—Steven M. Mitchell; Mark J. Meltzer

[57] ABSTRACT

An implantable cardioverter/defibrillator and method for its use. A sensing electrode provides an ECG signal to the defibrillator, this signal is amplified and evaluated for the presence of a tachyarrhythmia. The phase of the ECG signal is sensed during a detected fibrillation or tachycardia and this determines the phase of the stimulating output signals. The ECG may be continuously sensed during the application of the defibrillating output and each output is held constant until a threshold crossing of the ECG is detected, whereupon the defibrillating output is changed. The system may also be configured to generate outputs in response to the ECG signal exceeding one or more thresholds. The defibrillating output is generated as a constant current output. The ECG amplifier compensates for a resultant offset voltage with an autozero loop. The specific lead configuration and the patient's condition are considered in programming the amplitude and polarity of the defibrillation output. In an alternative embodiment, the phase of the ECG signal is detected and an output of predetermined duration is delivered. In this configuration, it is not necessary to sense the ECG during the output. The system may also be used in a preconditioning mode wherein the phase related output is followed by a conventional high voltage monophasic or biphasic defibrillation waveform. The ECG is monitored for return to normal rhythm and the output stimulation is discontinued when normal rhythm is restored.

27 Claims, 3 Drawing Sheets

METHOD AND APPARATUS FOR PHASE RELATED CARDIAC DEFIBRILLATION

FIELD OF THE INVENTION

The present invention relates generally to devices and methods for controlling cardiac arrhythmias, and more specifically to an implantable defibrillator and method of delivering defibrillating electrical signals to a patient's heart.

BACKGROUND OF THE INVENTION

A number of different systems and methods have been developed for delivering electrical shocks to a patient's heart for the treatment of detected abnormal heart rhythms (arrhythmias). These methods deliver specific waveform shapes or pulse sequences to the heart in order to treat the detected arrhythmia by depolarizing the heart tissue cells. One early waveform is disclosed in U.S. Pat. No. 3,706,313 to Milani et al., which provides a circuit for delivering a "trapezoidal" wave shape for defibrillating the heart by truncating the output of an exponentially decaying capacitor. Others have suggested the use of sequential pulses delivered through multiple pathways such as is described in U.S. Pat. No. 4,708,145 to Tacker, Jr. In Tacker, Jr., a series of rectangular or truncated exponential pulses are delivered to the heart using at least three electrodes. A first pulse is sent through a first pair of the three electrodes and then a second pulse is sent through a second, different pair of the electrodes. Still others have described the use of multiphasic waveforms, such as U.S. Pat. No. 4,637,397 to Jones et al., which describes a triphasic waveform. A triphasic waveform has three pulses of alternating positive and negative polarity. U.S. Pat. No. 3,924,641 to Weiss and U.S. Pat. No. 4,850,357 to Bach, Jr. describe the use of biphasic waveforms.

Defibrillation pulses of the type described above are typically in the range of from about 500 to 1000 volts delivered for a time of from about 2 to 12 milliseconds. Overall energy delivery to the heart for a defibrillation waveform may typically be from about 10 to 40 joules. A monophasic defibrillation waveform may typically be a truncated exponential decay with an initial voltage of about 700 volts and a duration of about 10 milliseconds. A biphasic defibrillation waveform may typically have an initial positive pulse of about 750 volts for a duration of 6 milliseconds and a negative pulse of about 100 to 400 volts for an equal duration. The leading edge voltage of the second pulse of a biphasic waveform may typically be equal to or one half of the trailing edge voltage of the initial pulse which itself depends on the tilt of the pulse. The overall energy delivered is a function of the voltage, duration, tilt and lead impedance.

Another modification of the standard waveform has been suggested by Imran in U.S. Pat. No. 4,768,512. That patent discloses a cardioverting system (defibrillation and cardioversion) in which a truncated exponential waveform is chopped at high frequencies to provide a voltage wave packet formed of a plurality of high-frequency cardioverting pulses with a preferred frequency in excess of 1 kHz.

Tachyarrhythmias, which are rapid but organized heart rhythms, may be treated with cardioversion pulses. These pulses are similar to defibrillation pulses but generally are delivered at lower voltages and are synchronous with the QRS complex. Pulses are delivered synchronously to help avoid accelerating a heart experiencing a ventricular tachyarrhythmia into ventricular fibrillation. Such a cardioverter is disclosed in U.S. Pat. No. 4,384,585 to Zipes. In Zipes, an implantable synchronous intracardiac cardioverter detects intrinsic depolarization of cardiac tissue and provides a shock to the heart in synchrony with the detected cardiac activity at a time when the bulk of cardiac tissue is already depolarized and in a refractory state. Synchronizing defibrillating pulses is not required since the heart is already in fibrillation when such pulses are delivered. Thus, some prior art defibrillators deliver defibrillation shocks to the heart without any correlation or synchronization to the timing of the sensed QRS complex from an electrocardiogram (ECG). Some other prior art devices synchronize such shocks to the QRS complex.

A primary goal in treating a detected tachyarrhythmia with an implantable cardioverter/defibrillator is to ensure delivery of effective therapy while minimizing energy delivery requirements for the defibrillation waveform. Lower voltage therapy is less painful and disruptive to the patient. Also, lower voltage electrical pulses allow for use of smaller batteries and capacitors even where the overall energy delivery is not reduced. Smaller batteries and capacitors result in a smaller implantable defibrillator.

SUMMARY OF THE INVENTION

The present invention provides an apparatus and method for cardiac defibrillation which utilizes a lower voltage defibrillation output to depolarize the myocardial cells by providing signals which have a phase which is related to the sensed ECG signal. A unipolar or bipolar sensing electrode provides an ECG signal to the defibrillator and this signal is amplified. The phase of the ECG signal is sensed during fibrillation to determine whether the signal is above or below predetermined thresholds and this determines the phase of the defibrillation output signal. In a preferred embodiment, the ECG is continuously sensed during the application of the defibrillating output signal and the output signal is held constant until a threshold crossing of the ECG is detected, whereupon the defibrillating output signal is changed. The defibrillating output signal is generated as a constant current signal in order to allow sensing during the defibrillating output since this produces a nearly constant voltage offset at the input to the ECG amplifier which is compensated for by an autozero loop in the sensing circuitry. It is possible to set one or more thresholds to create ranges of operation. Also, it is possible to set the thresholds to zero.

Depending on the specific lead configuration and the patient's condition, the amplitude and polarity of the defibrillation output signal can be adjusted. The output may be either monophasic (only positive or only negative pulses) or biphasic (both positive and negative pulses.) Thus, the defibrillator of the invention may generate a defibrillating output signal which is positive, negative or zero in response to ECG signals which are outside the thresholds. Examples of possible combinations are (1) positive detected ECG/positive delivered output signal—negative detected ECG/negative delivered output signal; (2) positive detected ECG/negative delivered output signal—negative detected ECG/positive delivered output signal; and (3) positive detected ECG/positive delivered output signal—negative detected ECG/zero delivered output signal.

In an alternative embodiment, the phase of the ECG signal is detected and a constant current output of predetermined duration is delivered. In this embodiment, it is not necessary to sense the ECG during the output. After the output terminates, the phase of the ECG is sensed again for delivery of the next output of predetermined duration. The duration of the output may be fixed or may be dependent upon one or more aspects of the arrhythmia, such as rate or duration of the arrhythmia. Each output may be either monophasic or biphasic. For this embodiment, a "biphasic" output is a single waveform having both a positive and a negative component.

In another embodiment of the invention, the phase related output signal is used to precondition the heart. This preconditioning output is then followed by a conventional defibrillation pulse.

In each of the embodiments of the invention, the ECG is monitored for return to normal rhythm and the output stimulation is discontinued when normal rhythm is restored.

The different embodiments of the invention may be used to treat tachycardia as well as fibrillation.

It is thus an object of the present invention to provide a method and apparatus for delivering defibrillation output stimulation which requires lower voltage than conventional defibrillation waveforms.

It is a further object of the invention to provide a method and apparatus for delivering defibrillation output stimulation which utilizes the heart's electrical signals to determine the phase of the defibrillation output.

BRIEF DESCRIPTION OF THE DRAWINGS

The various features and advantages of the present invention may be more readily understood with reference to the following detailed description taken in conjunction with the accompanying drawings and in which.

DETAILED DESCRIPTION OF THE INVENTION

Figure 1:
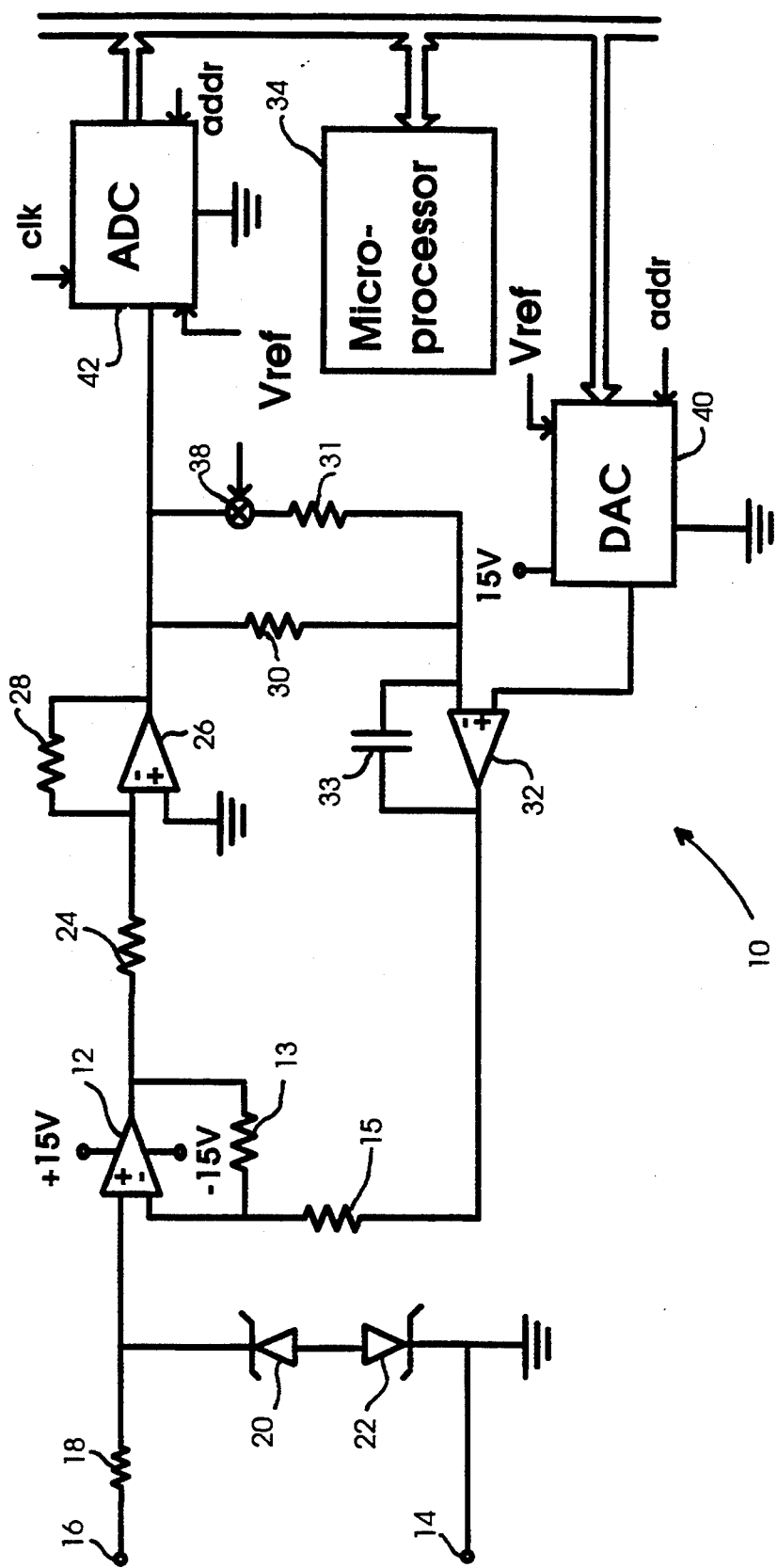
FIG. 1 shows a circuit diagram of the sensing portion of an implantable defibrillator constructed in accordance with the invention.

A preferred embodiment of the invention will now be described with reference to FIG. 1, wherein a sensing circuit 10 of the invention is shown. A relatively low gain input amplifier 12 with a pair of 33 kΩ resistors 13, 15 connected as shown is coupled to a patient's heart through sensing electrodes 14,16. Input components including a 10 kΩ resistor 18 and a pair of 12 V zener diodes 20, 22 protect the sensing circuit against damage in the event of a shock from a conventional external defibrillator. Input amplifier 12 has a high input impedance to avoid current flow through the electrode/electrolyte interface of sensing electrodes 14, 16 during the defibrillating output signal since current flow through the sensing electrodes could interfere with sensing during the application of the defibrillation output. As is known in the art, the sensing electrodes may also be used for bradycardia and antitachycardia pacing.

The output from amplifier 12 is coupled through an input resistor 24 having a value of 5 kΩ to a second amplifier 26 which has a comparatively high gain and includes a feedback resistor 28 having a value of 2.5 MΩ. The output from amplifier 26 is coupled to a DC baseline restoring circuit including a 22 MΩ input resistor 30, an amplifier 32 and a 0.22 μF capacitor 33. The baseline restoring circuit has a variable time constant controlled by a microprocessor 34 through switch 38. When switch 38 is closed, current from amplifier 26 is shunted through a 1.5 kΩ resistor 31 thus providing a faster time constant. Amplifier 32 has a variable DC set point which is set by an 8 bit autozero digital-to-analog converter (DAC) 40 which is also under control of microprocessor 34. As will be apparent to one skilled in the art, the circuit is a feedback loop, so compensation may be required for stability depending upon the actual components used.

The output from amplifier 26 is also coupled to a 12 bit analog-to-digital converter (ADC) 42 which samples at a clock rate of about 2.5 kHz. The use of a 12 bit ADC obviates the need for an automatic gain control circuit, but an automatic gain control circuit could be used.

Figure 2:
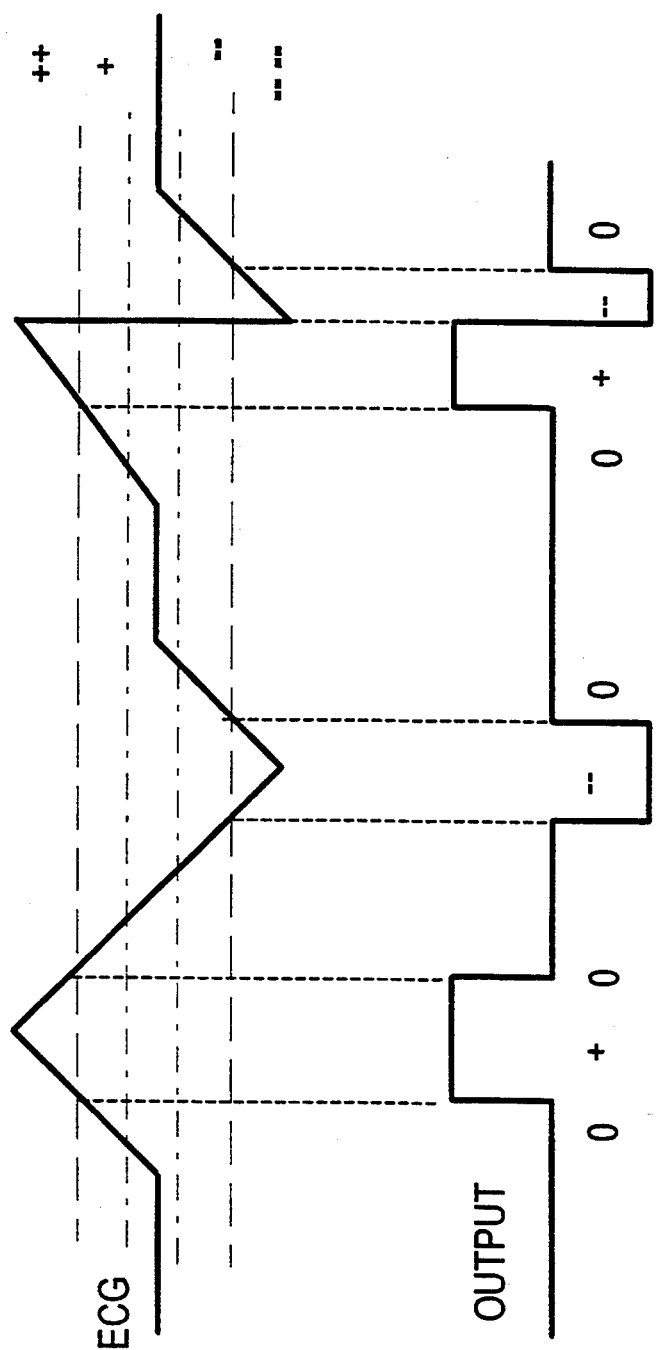
FIG. 2 is a graphical representation of the sensed ECG signal and the output pulses provided by one embodiment of the invention in response to those signals.

The operation of sensing circuit 10 will now be discussed with reference to a specific embodiment wherein a positive defibrillation output signal is generated in response to a positive ECG signal and a negative defibrillating output signal is generated in response to a negative ECG signal. Further, positive and negative digital thresholds are set as shown in FIG. 2. Only the upper positive and negative thresholds (designated "++" and "− −") are utilized to generate the output pulses shown in FIG. 2. The setting of the thresholds creates a deadband around ground potential where no output signal is generated by the microprocessor. In operation of the sensing circuit 10, the microprocessor 34 polls the ADC 42 to monitor the ECG signal from the patient's heart. Once fibrillation is detected, the ECG is monitored to determine if the signal has exceeded one of the preset digital thresholds. It will be understood that the invention may be used to treat tachycardia as well as fibrillation. The detection scheme used to determine the presence of a tachyarrhythmia may be any of those known in the art such as rate or morphology based schemes. Once the digital threshold is exceeded, for example by a positive ECG signal, the microprocessor commands a positive pulse output from the output stage (described below in connection with FIG. 3.) The output stage generates a constant current output which results in a constant voltage offset at the input to amplifier 12. It will be understood by those skilled in the art that the offset is not precisely constant due to impedance changes in the heart caused by motion, but these changes are slow compared to the electrical events, and minor particularly for a unipolar sensing configuration. Microprocessor 34 sets the autozero DAC 40 to the same potential as the ECG signal when it exceeded the positive digital threshold. Additionally, the microprocessor sets the DC baseline restoring circuit to the rapid time constant by closing switch 38. After a few milliseconds, the output of amplifier 26 is back to the same potential that it was at just prior to the application of the positive output signal. The microprocessor 34 then opens switches 38 to return the baseline restoring circuit to the slow time constant.

When the monitored ECG signal falls below the preset digital threshold during delivery of the positive stimulating pulse, the output from the output stage is shut off and the baseline restoring circuit again performs its autozero cycle with the autozero DAC set to the baseline value. If the ECG exceeds the negative digital threshold, a negative output is commanded by microprocessor 34 and the autozero cycle is repeated. Whenever an autozero cycle occurs, the autozero point is selected by microprocessor 34 to be near the digital threshold (or to the ECG value just prior to producing an output.) The output is made to go positive, negative, or is turned off in sequence, depending on the ECG signal as compared to digital thresholds, until the microprocessor detects that fibrillation has ceased, at which point no more output signals are produced.

Figure 3:
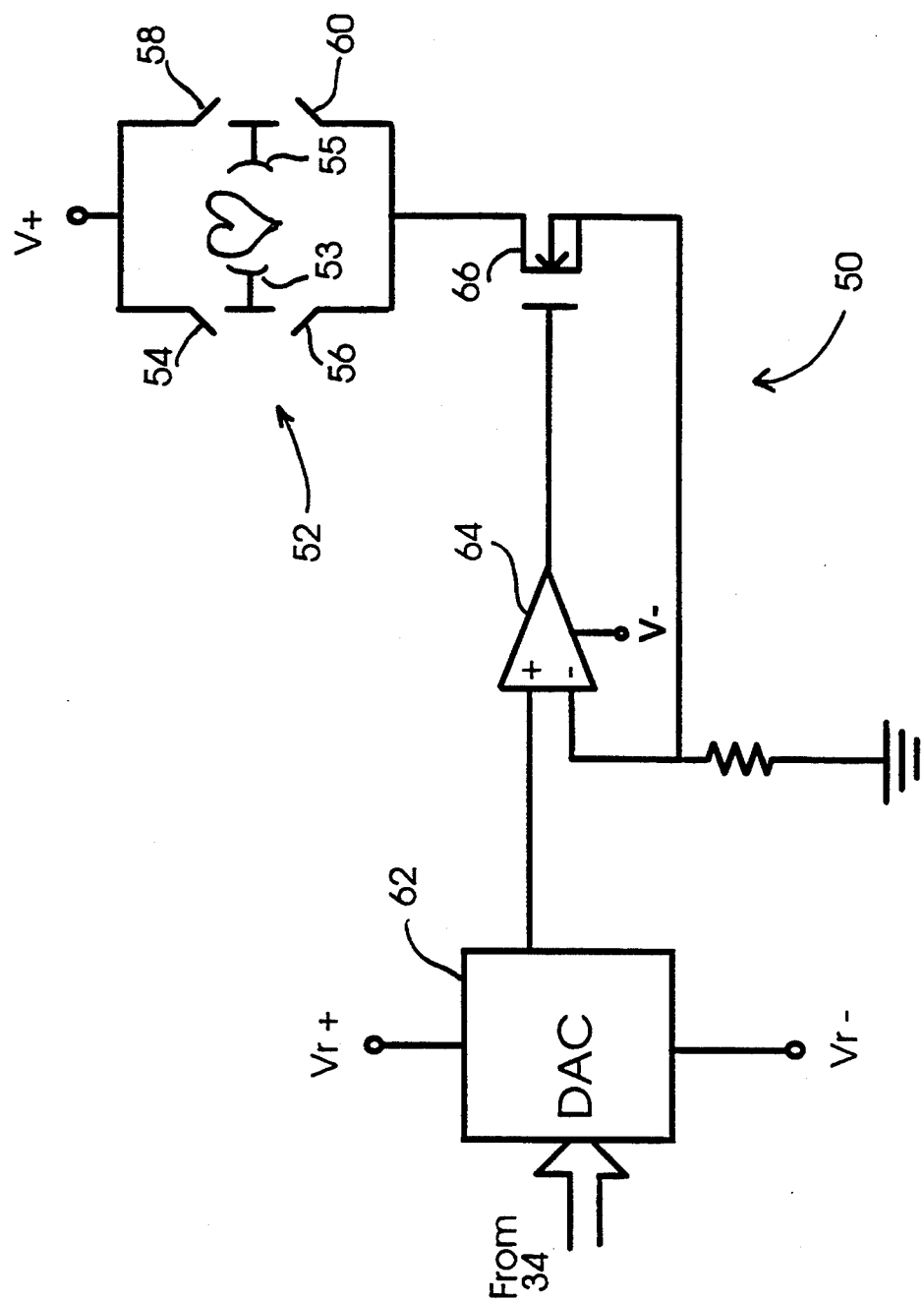
FIG. 3 shows a circuit diagram of the output stage of an implantable defibrillator constructed in accordance with the invention.

FIG. 3 shows a circuit diagram of an output stage 50 of an implantable defibrillator of the invention. A power supply V+ is the source for electrical stimulation output delivered to the patient's heart by an H-bridge circuit 52. The power supply is isolated from the sensing ground and thus from the sensing power supply to prevent pulse delivery from affecting the sensing circuit. The H-bridge is of the type disclosed in U.S. Pat. No. 3,924,641 to Weiss. Four switches 54, 56, 58 and 60 are controlled by microprocessor 34 and are configured to deliver either positive or negative phase output pulses to the patient's heart through a pair of defibrillation electrodes 53, 55. For example, when switches 54 and 60 are closed, a positive pulse is delivered through the defibrillation electrodes and when switches 58 and 56 are closed, a negative pulse is delivered defibrillation electrodes. One difference of the output stage of the invention from the circuit of Weiss is that the ground leg of the output stage of the invention has a programmable current source connected to it. A digital-to-analog converter (DAC) 62 receives input from microprocessor 34 setting the desired current to be delivered to the heart. This current typically can exceed 100 milliamps. A high precision op amp 64 controls the current flow through MOSFET 66 and minimizes current fluctuations in spite of electrode polarization and heart impedance changes. The microprocessor interfaces to the output stage 50 are all isolated, preferably using opto-isolators.

In an alternative embodiment of the invention, the system described above may be used in conjunction with a conventional defibrillation waveform. The phase related output signal is first delivered to precondition the heart. If this does not cause the heart to revert to a normal rhythm, a conventional monophasic or biphasic cardioversion or defibrillation pulse is delivered through the H-bridge. This may be accomplished either by setting the current source to a higher or maximum output and delivering the waveform for a predetermined time or by providing the high voltage defibrillation waveform with circuitry known in the prior art such as is described in U.S. Pat. No. 5,111,816 to Pless et al. which is assigned to the assignee of the present application and which is incorporated herein by reference. In the case of separate power supply circuits for delivery of the phase related output for preconditioning and the conventional defibrillation waveform, the H-bridge circuit would be shared. The use of two separate power supplies may be preferable due to the fact that the charging time required to recharge the capacitors of the phase related output circuit power supply may create a larger than desired delay before the power supply would be ready for delivery of the conventional waveform.

As mentioned above, numerous configurations of output signals are possible in practicing the invention. The following table provides the possible configurations where a pair of positive thresholds and a pair of negative thresholds are set. In the table, "z" means high impedance or no output. The column designated "++" is the output for signals above the upper positive threshold and the column "+" is the output for ECG signals between the upper and lower positive thresholds. Any signals between the lower positive threshold and the lower negative threshold are in the "deadband" region and in all cases of the preferred embodiments of the invention the output pulse is zero in response to ECG signals in the deadband region. Similar nomenclature applies for negative ECG signals. The thresholds of the table are graphically represented in FIG. 2 which presents the output of configuration 1 in the table.

| Output | ECG polarity ++ | + | dead band | - | -- |
|---|---|---|---|---|---|
| 1 | + | z | z | z | - |
| 2 | - | z | z | z | + |
| 3 | + | z | z | z | z |
| 4 | - | z | z | z | z |
| 5 | z | z | z | z | - |
| 6 | z | z | z | z | + |
| 7 | z | + | z | - | z |
| 8 | z | - | z | + | z |
| 9 | z | + | z | z | z |
| 10 | z | - | z | z | z |
| 11 | z | z | z | + | z |
| 12 | z | z | z | - | z |

Any one of these configurations may be programmed using conventional programming techniques for an implantable cardioverter/defibrillator. Additionally, other threshold configurations are possible including setting of the thresholds to zero.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A medical device for electrically stimulating a patient's heart comprising:
    means for sensing electrical signals from said patient's heart;
    means for determining a polarity of said sensed electrical signals; and
    means for generating at least one electrical output for delivery to said patient's heart, wherein said output has a polarity which is based on the determined polarity of said sensed electrical signals.

2. A medical device according to claim 1 wherein said means for sensing includes a sensing lead having a sensing electrode and further includes an amplifier for receiving and amplifying signals from said sensing lead.

3. A medical device according to claim 1 wherein said means for generating at least one electrical output includes means for generating a series of electrical outputs.

4. A medical device according to claim 1 wherein said means for generating at least one electrical output includes means for generating an electrical output having a predetermined duration.

5. A medical device according to claim 1 and further including means for generating a defibrillation waveform which is not based on the determined polarity of said sensed electrical signals.

6. An implantable cardioverter/defibrillator for treating tachyarrhythmias comprising:
   a sensor adapted to be coupled to a patient's heart for sensing ECG signals;
   a sensing circuit coupled to receive said ECG signals for detecting presence of a tachyarrhythmia and for determining a polarity of said ECG signals; and
   an output generating circuit for generating a plurality of electrically stimulating outputs in response to a detected tachyarrhythmia, each of said outputs having a polarity which is based on the determined polarity of said ECG signals.

7. An implantable cardioverter/defibrillator according to claim 6 wherein said output generating circuit includes a constant current output circuit.

8. An implantable cardioverter/defibrillator according to claim 6 wherein said output generating circuit includes thresholding means for triggering the generation of said stimulating outputs when an amplitude of said ECG signals exceeds one or more predetermined thresholds.

9. An implantable cardioverter/defibrillator according to claim 6 wherein said output generating circuit includes means for delivering each output for a predetermined time.

10. An implantable cardioverter/defibrillator for treating tachyarrhythmias comprising:
    a sensor adapted to be coupled to a patient's heart for sensing ECG signals;
    a sensing circuit coupled to receive said ECG signals for detecting presence of a tachyarrhythmia and for determining a polarity of said ECG signals;
    an output generating circuit for generating a plurality of electrically stimulating outputs in response to a detected tachyarrhythmia, each of said outputs having a polarity which is based on the determined polarity of said ECG signals, said output generating circuit including a constant current output circuit; and
    said sensing circuit including an input amplifier having an amplifier and an autozero loop coupled to said input amplifier to compensate for a voltage offset at said input of said input amplifier.

11. An implantable cardioverter/defibrillator according to claim 10 wherein said sensing circuit further includes means for adjusting a time constant of said autozero loop.

12. A medical device for electrically stimulating a patient's heart comprising:
    a sensing lead for sensing electrical signals from said patient's heart;
    an amplifier coupled to receive an input signal from said sensing lead and provide an amplified ECG signal;
    a circuit for determining a polarity of said amplified ECG signal; and
    an output delivery circuit adapted to be coupled to said patient's heart for delivering at least one electrical output, said electrical output having a polarity which is based on the determined polarity of said ECG signal.

13. A medical device according to claim 12 and further including a detector coupled to receive said ECG signals and adapted to determine presence of a heart arrhythmia and initiate delivery of said electrical output from said output delivery circuit and to detect a return of said patient's heart to a normal rhythm and discontinue output delivery in response thereto.

14. A medical device according to claim 13 wherein said detector comprises a microprocessor.

15. A medical device according to claim 12 wherein said output delivery circuit includes means for delivering a constant current output.

16. A medical device according to claim 12 wherein said output delivery circuit includes means for delivering said electrical output for a predetermined time.

17. A medical device according to claim 12 wherein said output delivery circuit includes a microprocessor and at least two defibrillation leads and a plurality of delivery switches connected to and controlled by said microprocessor.

18. A medical device for electrically stimulating a patient's heart comprising:
    a sensing lead for sensing electrical signals from said patient's heart;
    an amplifier having an input coupled to receive an input signal from said sensing lead and provide an amplified ECG signal;
    a circuit for determining a polarity of said amplified ECG signal;
    an output delivery circuit adapted to be coupled to said patient's heart for delivering at least one electrical output, said electrical output having a polarity which is based on the determined polarity of said amplified ECG signal, said output delivery circuit including a constant current output circuit; and
    an autozero loop coupled to said amplifier to compensate for a voltage offset at said input of said amplifier.

19. An implantable defibrillator system for providing polarity coherent defibrillation stimulation to a patient's heart comprising:
    an endocardial sensing lead adapted to be connected to said patient's heart;
    an amplifier having an input coupled to said sensing lead and providing an amplified ECG signal;
    a polarity sensing circuit;
    pulse delivery switch circuitry;
    pulse delivery leads coupled to said pulse delivery switch circuitry having at least a pair of electrodes adapted to be positioned proximate said patient's heart; and
    a controller coupled to said pulse delivery switch circuitry for delivering pulses to said patient's heart through said pulse delivery leads, said pulses having a polarity which is based on a polarity of said ECG signal detected by said polarity sensing circuit.

20. An implantable defibrillator system according to claim 19 and further including a detector coupled to receive the amplified ECG signal from said amplifier to detect presence of an arrhythmia.

21. A method for treating a tachyarrhythmia comprising the steps of:
    sensing an electrical signal from a patient's heart;
    determining a polarity of said sensed signal;
    generating a plurality of electrical pulses each with a polarity based on the polarity of said sensed signal; and
    applying said plurality of pulses to said patient's heart.

22. The method of claim 21 wherein said generating step provides no pulse in response to one polarity of said sensed electrical signal.

23. The method of claim 21 and further including the steps of:
   detecting a return of said patient's heart to a normal rhythm; and
   discontinuing the application of said pulses to said patient's heart.

24. The method of claim 21 wherein each of said pulses has a predetermined duration and wherein each subsequent pulse of said plurality of electrical pulses has its polarity determined as a function of the polarity of the sensed signal after the conclusion of the previous pulse.

25. The method of claim 24 and further including the steps of:
   detecting a return of said patient's heart to a normal rhythm; and
   discontinuing the application of pulses to said patient's heart.

26. The method of claim 21 and further including the step of setting a positive and a negative threshold for said polarity determining step to create a deadband and generating said pulses only when said electrical signal is outside said deadband.

27. The method of claim 21 and further including the steps of:
   discontinuing said plurality of pulses after a predetermined time;
   generating a defibrillation waveform which is not based on the determined polarity of said sensed signal; and
   applying said defibrillation waveform to said patient's heart.

* * * * *